United States Patent [19]
Levy et al.

[11] Patent Number: 6,099,846
[45] Date of Patent: *Aug. 8, 2000

[54] ENHANCEMENT OF B CELL LYMPHOMA AND TUMOR RESISTANCE USING IDIOTYPE/CYTOKINE CONJUGATES

[75] Inventors: Ronald Levy, Stanford, Calif.; Mi-Hua Tao, Taipei, Taiwan

[73] Assignee: The Board of Trustees of the Leland Stanford Junior University, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/416,787

[22] PCT Filed: Oct. 14, 1993

[86] PCT No.: PCT/US93/09895

§ 371 Date: Apr. 14, 1995

§ 102(e) Date: Apr. 14, 1995

[87] PCT Pub. No.: WO94/08601

PCT Pub. Date: Apr. 28, 1994

Related U.S. Application Data

[63] Continuation-in-part of application No. 07/961,788, Oct. 14, 1992, abandoned.

[51] Int. Cl.$^7$ .................................................. A61K 39/385
[52] U.S. Cl. .................................... 424/195.11; 424/85.1; 424/85.2; 424/180.1; 530/351; 530/387.3
[58] Field of Search .................................. 424/85.8, 85.1, 424/85.2, 131.1, 152.1, 178.1, 179.1, 180.1, 193.1, 194.1, 195.11; 435/69.1, 91, 252.3, 320; 530/387.3, 350, 351, 387.1, 387.2, 391.1, 391.5, 806, 808; 536/125.35

[56] References Cited

U.S. PATENT DOCUMENTS 5,281,699  1/1994  Chang ...................................... 530/404

OTHER PUBLICATIONS

Morrissey, P.J., et al., "Granulocyte–macrophage colony–timulating factor augments the primary antibody response by enhancing the function of antigen presenting cells" *J. Immunol.* (1987) 139:1113–1119.

Hinuma, S., et al., "A novel strategy for converting recombinant viral protein into high immunogenic antigen" *FEBS Letters* (1991) 288:138–142.

Taylor–Papadimitriou, J., et al., "Fusion potential for vaccines" *Nature* (1993) 362:695.

Ahmad, A., et al., "Recombinant targeted proteins for biotherapy" *Mol. Biother.* (1990) 2:67–73.

Campbell, M.J., et al., "Immunotherapy of established murine B cell lymphoma. Combination of idiotype immunization and cyclophosphadine " *J. Immunol.* (1988) 141:3227–3233.

Campbell, M.J., et al., "Idiotype vaccination against murine B cell lymphoma" *J. Immunol.* (1990) 145:1029–1036.

Gillies, S.D. et al., "Biological activity and in vivo clearance of antitumor antibody/cytokine fusion proteins" *Bioconjugate Chem.* (1993) 4:230–235.

Kaminski, M.S., et al., "Idiotype vaccination against murine B cell lymphoma. Inhibition of tumor immunity by free idiotype protein" *J. Immunol.* (1987) 138:1289–1296.

Kwak, L.W., et al., "Induction of immune responses in patients with B–cell lymphoma against the surface–immunoglobulin idiotype expressed by their tumors" *New Engl. J. Med.* (1992) 327:1209–1215.

Osband, M.E. et al., "Problems in the investigational study and clinical use of cancer immunotherapy" *Immunol. Today* (1990) 11:193–195.

Roitt et al., Immunology 3rd Edition, Mosby Publications, Jan. 1993.

Kuby. Immunology. W.H. Freeman and Company. New York pp. 248,257–258, Jan. 1992.

*Primary Examiner*—Christina Y. Chan
*Assistant Examiner*—Patrick J. Nolan
*Attorney, Agent, or Firm*—Morrison & Foerster LLP

[57] ABSTRACT

B cell lymphoma tumor-associated antigen or a fragment thereof containing an epitope are linked to an immune-enhancing cytokine, such as GM-CSF, IL-2, or IL-4 to form an immuno-complex. This immuno-complex elicits immune responses which are protective with respect to tumor proliferation. The linkers may be simple chemical bifunctional moieties introduced through chemical synthetic techniques or peptides introduce through recombinant methodologies. Antibodies immunoreactive with these immunocomplexes are also useful as passive vaccines and as analytical tools.

7 Claims, 10 Drawing Sheets

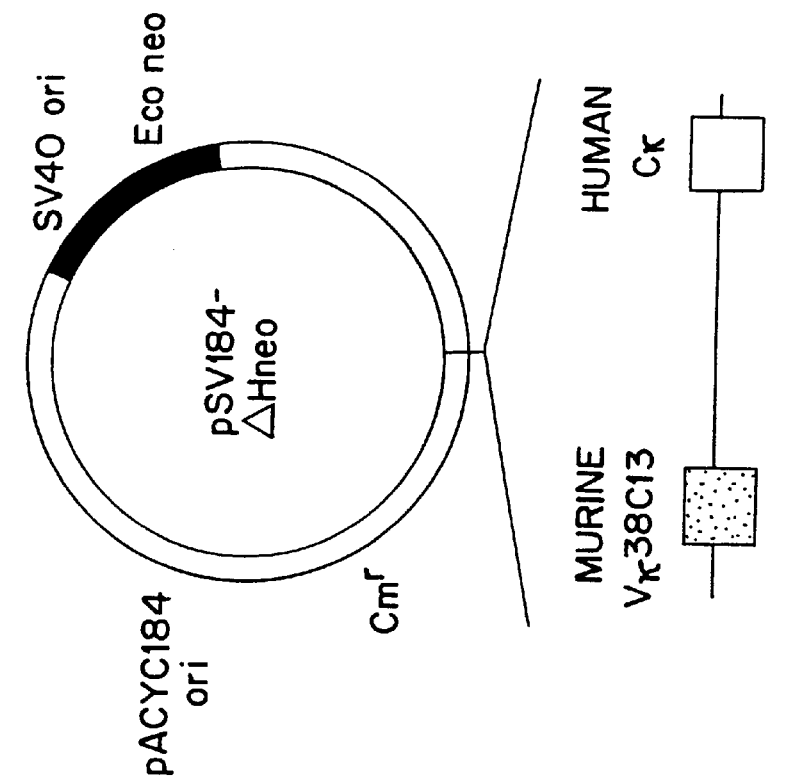
FIG.IB
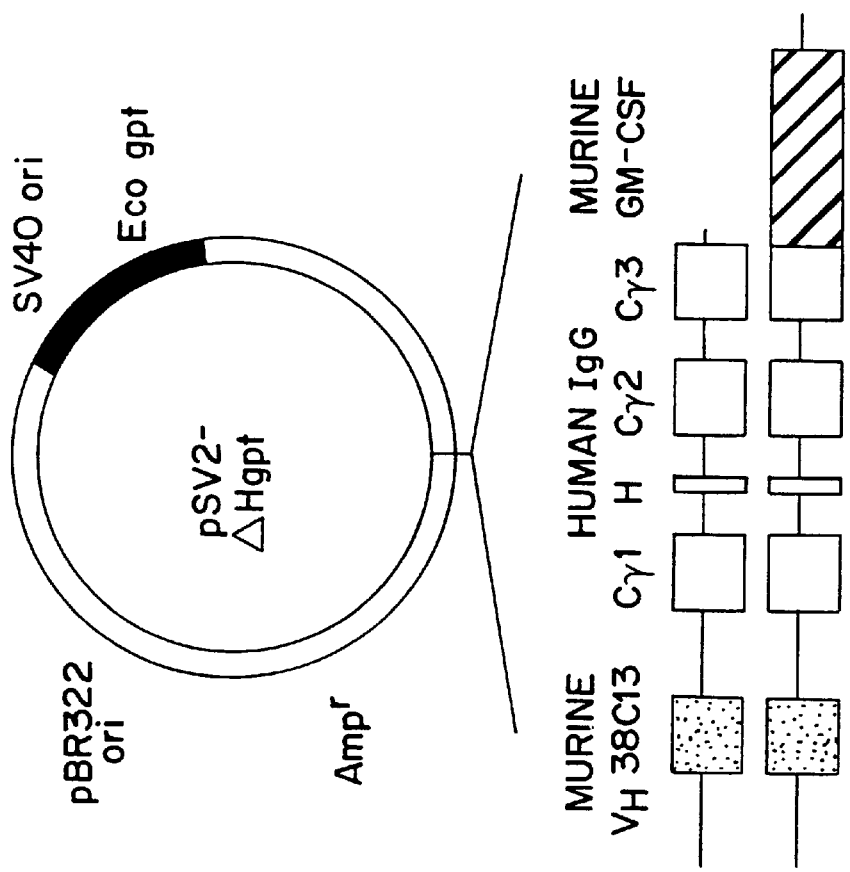
FIG.IA

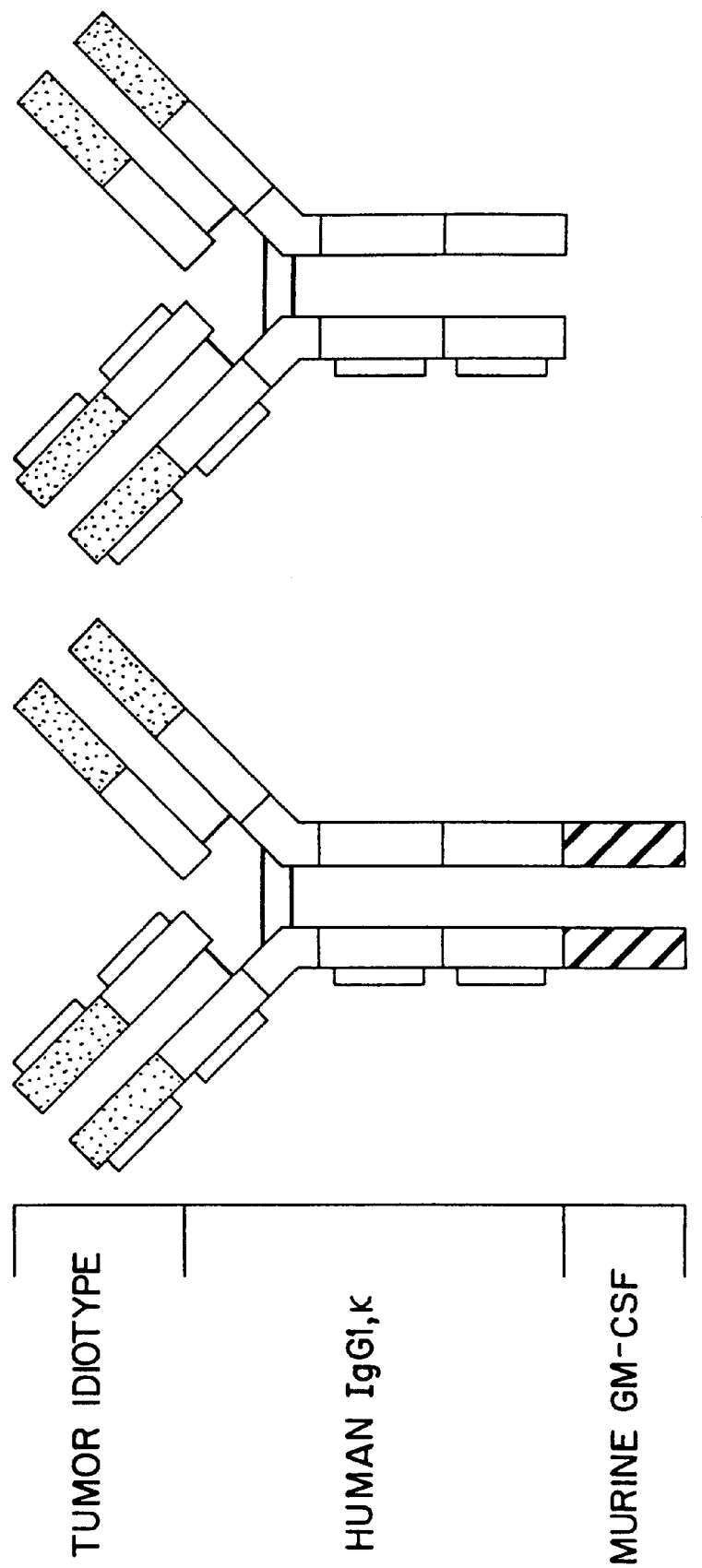

ENHANCEMENT OF B CELL LYMPHOMA AND TUMOR RESISTANCE USING IDIOTYPE/CYTOKINE CONJUGATES

CROSS-REFERENCE TO RELATED APPLICATIONS

This application is a 35 U.S.C. §371 filing of International Patent Application No. PCT/US93/09895, which is a continuation-in-part of U.S. Ser. No. 07/961,788, filed Oct. 14, 1992, now abandoned.

TECHNICAL FIELD

The invention relates to the field of modulating B cell lymphoma tumor growth using immunological methods. More specifically, the invention concerns use of immunological constructs to confer resistance to B cell lymphoma tumors, and to enhance immune response.

BACKGROUND ART

Malignant tumors often express characteristic antigens or "markers" which offer a mechanism for tumor prevention, resistance or treatment. The antigens which are characteristic of the tumor may be purified and formulated into vaccines. This may stimulate an antibody response and a cellular immune response which are helpful in controlling tumor growth. At a minimum, the antibodies raised by these antigens can be used as detection tools to monitor the level of tumor marker in the host to track the course of the disease or the effectiveness of treatment.

It is well known that the immunogenicity of antigens can be enhanced by coupling these hapten-bearing moieties to carriers. A variety of carriers are routinely used, such as keyhole limpet hemocyanin and various serum albumins. It is also understood that certain cytokines, such as GM-CSF, have the capacity to enhance primary antibody responses to antigens (Morrissey, P. J., et al, *J Immunol* (1987) 139: 1113–1119).

The immune response-enhancing ability of a cytokine, when coupled to a viral antigen, has been shown by Hinuma, S., et al, *FEBS* (1991) 288: 138–142. In this work, interleukin-2 was coupled to a herpes simplex virus type I glycoprotein by generating a fusion protein consisting of the glycoprotein D and human IL-2. The conjugate was shown to induce high antibody responses and cell-mediated immunity to HSV-I in mice.

It has now been found that B cell lymphoma tumor-associated antigens can be coupled to immune response-enhancing cytokines, such as GM-CSF, IL-2 and IL-4, to produce an immune response to the tumor antigen and enhance the ability of the host to resist tumor growth associated with the antigen.

DISCLOSURE OF THE INVENTION

The invention provides compositions and methods for the modulation of B cell lymphoma tumor growth where the tumor is characterized by an associated antigen carrying an epitope which is characteristic of the tumor. The immunogenicity of preparations of the antigen used to raise antibodies and stimulate an immune response can be enhanced by coupling the antigen to an appropriate cytokine. The conjugate is superior in effect to the antigen coupled to conventional immunogenic carriers.

In one aspect, the invention is directed to an immunocomplex, which complex comprises a B cell lymphoma tumor-associated antigen covalently coupled to an immune-enhancing cytokine. The complex may be obtained by generating the antigen and the cytokine as a fusion protein using recombinant techniques; thus, in another aspect, the invention is directed to recombinant materials and methods for production of such fusion proteins. In still other aspects, the invention is directed to pharmaceutical compositions and vaccines containing the immunogenic complexes of the invention and to methods of conferring antitumor immunity using these complexes. In still other aspects, the invention is directed to antibodies generated by immunization with the complexes of the invention and to antibodies immunospecific to the conjugates. The invention is also directed to methods to confer immunity by administering polyclonal or monoclonal preparations of antibodies generated by the conjugates.

It has also been found that the immune-enhancing cytokine activity is improved by extending or coupling the cytokine to an additional moiety. Accordingly, in another aspect, the invention is directed to enhancing the activity of a cytokine by coupling to an additional moiety.

BRIEF DESCRIPTION OF THE DRAWINGS

FIG. 1A shows diagrammatically the construction of expression vectors for a B cell lymphoma tumor antigen Ig heavy chain coupled to murine GM-CSF;

FIG. 1B shows diagrammatically the construction of an expression vector for the light chain of this tumor-associated antigen.

FIG. 2 shows diagrammatically the products of transformed mouse myeloma cells transfected with the vectors illustrated in FIGS. 1A and 1B.

MODES OF CARRYING OUT THE INVENTION

Figure 3:
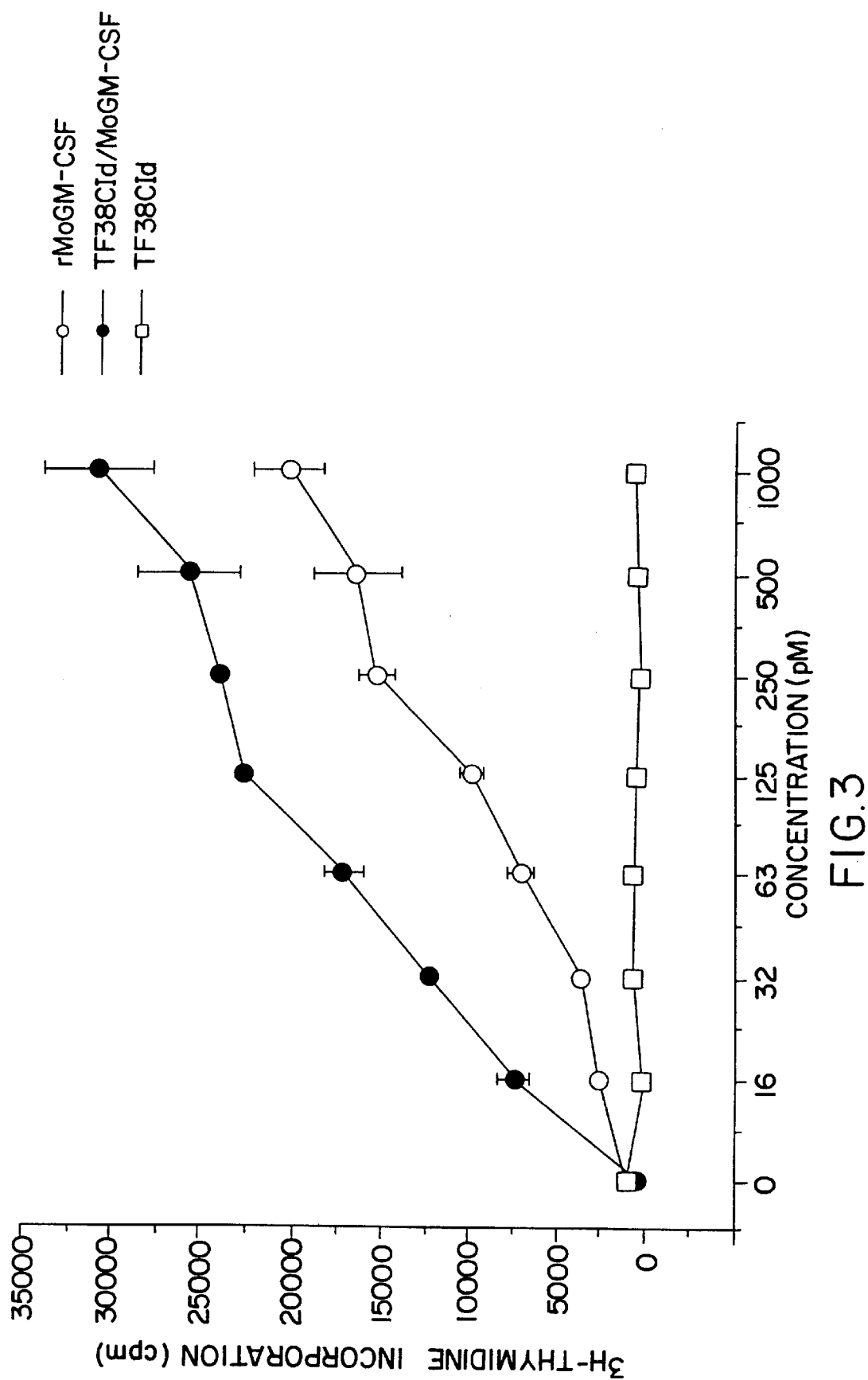
FIG. 3 is a graph showing the ability of GM-CSF-coupled antigen to support the proliferation of a GM-CSF-dependent cell line.

The invention provides B cell lymphoma antitumor vaccines of enhanced immunogenicity wherein the active ingredient is an immunocomplex containing an immune-enhancing cytokine covalently bound to a B cell lymphoma tumor-associated antigen or a fragment thereof containing at least one epitope characteristic of the tumor.

By "tumor-associated antigen" is meant a proteinaceous molecule containing at least one epitope wherein the epitope characterizes the tumor and is unique to the tumor as opposed to other tissues. The nature of the tumor-associated antigen will, of course, vary with the nature of the tumor. For B-cell lymphomas, the tumor-associated antigen is most frequently an immunoglobulin. The use of such tumor-associated antigens to produce monoclonal anti-idiotype antibodies has been described in U.S. Pat. No. 4,661,586 and U.S. Pat. No. 4,816,249. An assay for the monoclonal antibodies against tumor surface immunoglobulins is described and claimed in U.S. Pat. No. 4,513,088. The disclosure of these patents is incorporated herein by reference.

By "immune-enhancing cytokine" is meant a cytokine that is capable of enhancing the immune response when the cytokine is generated in situ or is administered to a mammalian host. Such cytokines are well known in the art and have become numerous. They include GM-CSF, IL-2, IL-3, and IL-4.

The immune-enhancing activity of cytokines can also be improved by their extension with additional moieties. As shown in Example 2, a cytokine coupled to an additional molecular structure is more effective in stimulating proliferation of NFS-60 cells than the cytokine alone. Such additional molecular structure is variable, and may comprise additional copies of the cytokine itself.

The tumor-associated antigen or the relevant epitope-bearing portion thereof may be coupled to the immune-enhancing cytokine using conventional coupling techniques such as coupling with dehydrating agents such as ECDI, dicyclohexylcarbodiimide (DCCI), and the like. In addition, commercially available or other synthetic linkers may be used in standard chemical coupling techniques. Such linkers, which are capable of coupling through sulfhydryl groups, amino groups, or carboxyl groups, are available from Pierce Chemical Co. (Rockford, Ill.). If the tumor-associated antigen or cytokine contains glycosylation, coupling can also be effected through the carbohydrate moieties using, for example, reductive amination. A wide variety of standard coupling techniques for covalent binding of the B cell lymphoma tumor-associated antigen with the cytokine is known in the art.

The B cell lymphoma tumor-associated antigen may be obtained by purification from the tumor or may be synthesized using recombinant techniques. In the case of the B-lymphomas, the immunoglobulin antigen may be affinity purified using, for example, protein A or other suitable means. A wide variety of cytokines is available in the art, and the genes for many of the cytokines have been cloned so that recombinant production of the cytokine portion of the complex may also be effected.

Alternatively, the immunocomplex can be constructed recombinantly as a fusion protein using the genes encoding the B cell lymphoma tumor-associated antigen and the immune-enhancing cytokine. Such fusions can be constructed by ligating DNAs encoding each protein in reading frame and coupling these to standard expression systems, as is by now generally known in the art. In general, it is preferred to produce the fusion proteins in mammalian host cells, although procaryotic or yeast expression is also feasible. The choice of control sequences that will be operably linked to the DNA encoding the fusion protein will depend on host choice, and the wide availability of control sequences for selected hosts is by now well known.

The immunocomplexes of the invention can then be used to engender an immune response in the host to be protected against the tumor. Generally, the immunocomplex is administered by injection—intravenous, intramuscular, intraperitoneal and the like—along with a suitable vehicle and excipient for injection. Suitable formulations for injection, including appropriate adjuvants, can be found, for example, in *Remington's Pharmaceutical Sciences*, Mack Publishing Company, Easton, Pa., latest edition. Protocols for administration can be formulated using routine optimization techniques, whereby repeated administration and concomitant antibody titering of the serum is performed until suitable titers are obtained. The polyclonal antisera produced by administration of the immunocomplexes of the invention can also be used for passive immunization of hosts against tumor proliferation. Preferably, however, the antibody-producing cells of the immunized host are immortalized, for example, using the standard fusion techniques of Kohler and Milstein, and the resulting immortalized cells are screened for production of antibodies which are immunoreactive with the B cell lymphoma tumor-associated antigen.

By "immunoreactive with the B cell lymphoma tumor-associated antigen" is meant that the antibodies have sufficiently high affinity for such antigens to detect them in standard assay systems. Such polyclonal or monoclonal antibodies are also useful in passive immunization.

Antibodies will also be produced which are immunospecific for the immunocomplexes. By "immunospecific for the immunocomplex" is meant that the antibodies recognize the immunocomplex as distinct from the components thereof. These immunospecific antibodies are useful in monitoring the levels of immunocomplex circulating in the plasma as well as in monitoring the production of the immunocomplex by expression of the appropriate recombinant systems. These antibodies may also be conveniently used for purification of the immunocomplex from the production vessels.

The following examples are intended to illustrate but not to limit the invention.

EXAMPLE 1

Construction of Idiotype/GM-CSF Fusion Protein

A carcinogen-induced murine B-cell tumor, 38C13, was used as the source of tumor-derived idiotypic protein. Immunoglobulins produced by this tumor, 38CId, have been used in immunization protocols and shown to be effective in protecting animals from subsequent lethal tumor challenge. In these immunizations, the antigen was coupled to standard immunogenic carriers such as KLH.

The $V_H$ and $V_L$ genes of the 38C13 tumor cells were cloned using the polymerase chain reaction (PCR) and ligated to human Igγ and Igκ constant region genes in the heavy- and light-chain expression vectors pSV2-ΔHGPT and pSV184-ΔHneo, respectively. The murine GM-CSF gene was cloned by PCR and ligated to the Cγ3 exon of the heavy-chain gene. The construction of these vectors is shown diagrammatically in FIGS. 1A and 1B, respectively. FIG. 1A shows diagrammatically the coupling of the $V_H$ region of 38C13 and the Cγ1, H, Cγ2, and Cγ3 regions of human IgG. The heavy-chain DNA is constructed including or not including the coding sequence for murine GM-CSF. The constructs are then inserted into the host vector as shown.

FIG. 1B shows the coupling of the murine $V_\kappa$ 38C13 with the human $C_\kappa$ constant region. The hybrid gene is ligated into pSV184-ΔHneo under control of the host vector promoter.

Both plasmids are then transfected by electroporation into the Ig-deficient murine plasma-cytoma cell line AG8.653 for expression. The culture supernatants were screened for production of the chimeric proteins using a standard ELISA assay, and the chimeric proteins were purified by protein-A chromatography.

FIG. 2 shows diagrammatically the proteins produced. TF38CId is the tumor-associated antigen comprising the tumor idiotype coupled with constant regions derived from human immunoglobulins. TF38CId/MoGM-CSF is identical, except for the fusion to murine GM-CSF. The chimeric proteins secreted by the murine myeloma cells were analyzed by reducing and nonreducing SDS-PAGE. Analysis of the results showed that TF38CId/MoGM-CSF was expressed as a molecule with a molecular weight of 210 kd.

EXAMPLE 2

Ability of the Fusion Protein to Retain Immune Enhancement

Proliferation assays were conducted by plating GM-CSF-dependent NFS-60 cells with various concentrations of test compound. The cells were incubated for 18 hours and the proliferation determined by standard labeled thymidine-incorporation assay.

FIG. 3 shows the results of this assay. The graph in FIG. 3 plots thymidine incorporation in counts per minute (Y-axis) against the concentration in pM (X-axis). Treatment with TF38CId alone (□) provides no stimulation of proliferation; treatment with recombinant murine GM-CSF alone (○) shows intermediate ability to proliferate; treatment with the fusion protein of the invention, TF38-CId/MoGM-CSF (●) shows greatly enhanced ability to stimulate proliferation in a dose-dependent fashion.

The ability of the fusion protein to stimulate cell proliferation could, as expected, be inhibited by antibodies raised against GM-CSF and, to a lesser extent, by antibodies raised against the constant heavy chain to which the GM-CSF is fused. In this assay, NFS-60 cells were incubated with 250 pM of the fusion protein and with various antibodies. The proliferation was determined by thymidine uptake, as above.

Figure 4:
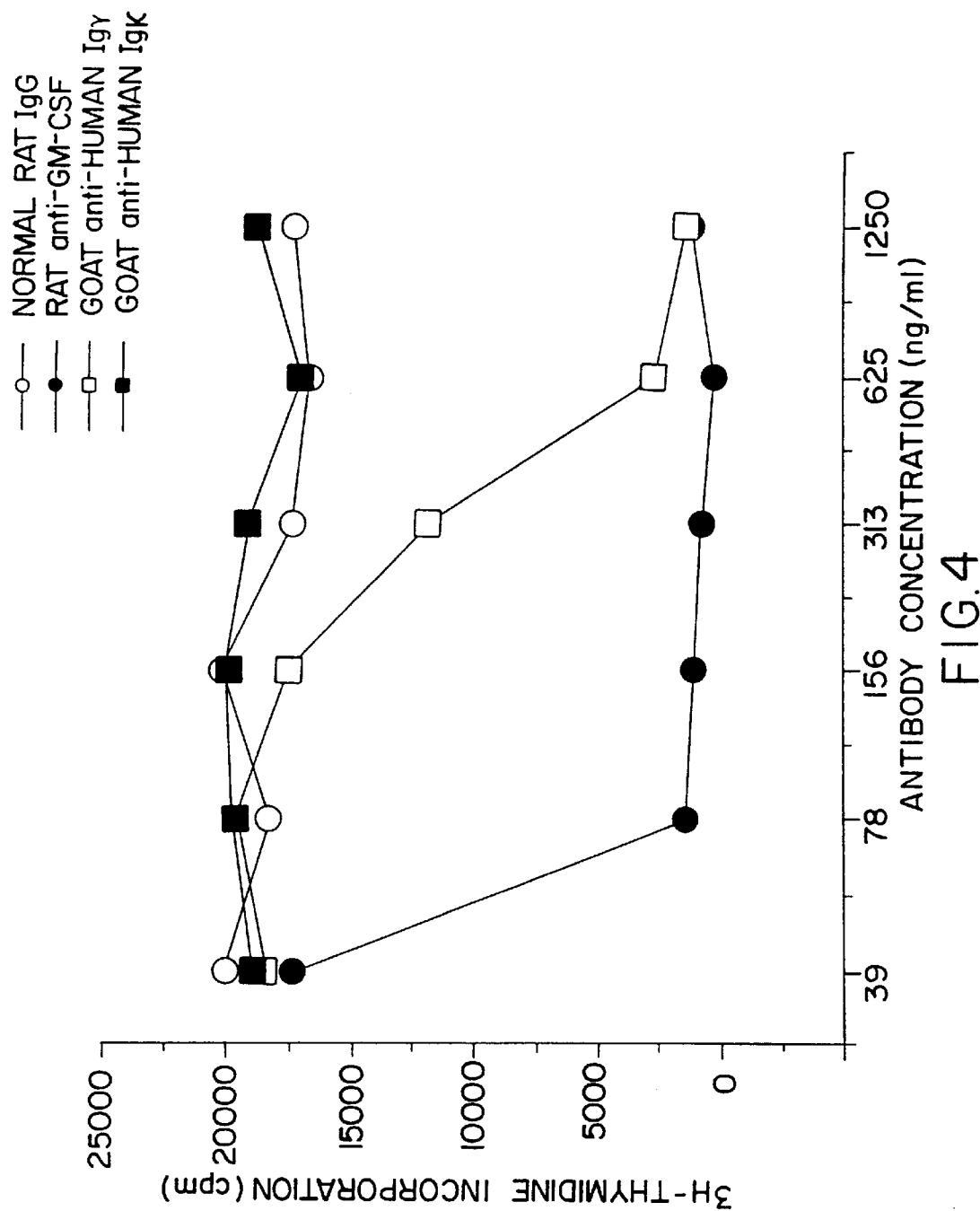
FIG. 4 is a graph which shows the ability of antibodies produced against GM-CSF to inhibit the proliferative activity of the immunocomplex.

FIG. 4 shows the results of these assays where antibody concentration in ng/ml is plotted on the X-axis against thymidine incorporated on the Y-axis. As shown, neither antibodies to human constant κ-chain (■) or to normal rat immunoglobulin (○) were able to inhibit the proliferation of NFS-60 cells stimulated by the fusion protein of the invention. However, proliferation was almost completely inhibited by 78 ng/ml rat anti-GM-CSF (●) and, to a lesser extent, by goat antihuman Ig-γ (□) wherein 625 ng/ml of these antibodies diminished proliferation almost to zero.

EXAMPLE 3

Ability of the Fusion Protein to Immunize Mice

Groups of C3H/HeN mice were immunized twice intraperitoneally with either KLH-conjugated TF38CId, unconjugated TF38CId, TF38CId mixed with recombinant murine GM-CSF, or with the fusion protein of the invention, TF38CId/MoGM-CSF. The immunogens were administered at days −28 and −14 before tumor challenge at day 0. The animals were bled at days −18 and −4 and anti-idiotypic antibodies determined by ELISA against native 38CId (mouse IgM, κ). The antibody titers are shown in Table 1.

TABLE 1

| IMMUNOGEN | ANTI-ID (μg/ml ± SD) DAY (−18) | ANTI-ID (μg/ml ± SD) DAY (−4) |
|---|---|---|
| KLH-conjugated TF38CId | 23 ± 14 | 296 ± 207 |
| TF38CId | 0 | 0 |
| TF38CId & rMOGM CSF Mixture | 0 | 0 |
| TF38CId/MoGM-CSF | 55 ± 39 | 152 ± 139 |

As seen in the table, both the KLH-conjugated idiotype and the protein of the invention raised substantial antibody titers; the KLH-conjugated complex was slightly more effective.

Figure 5:
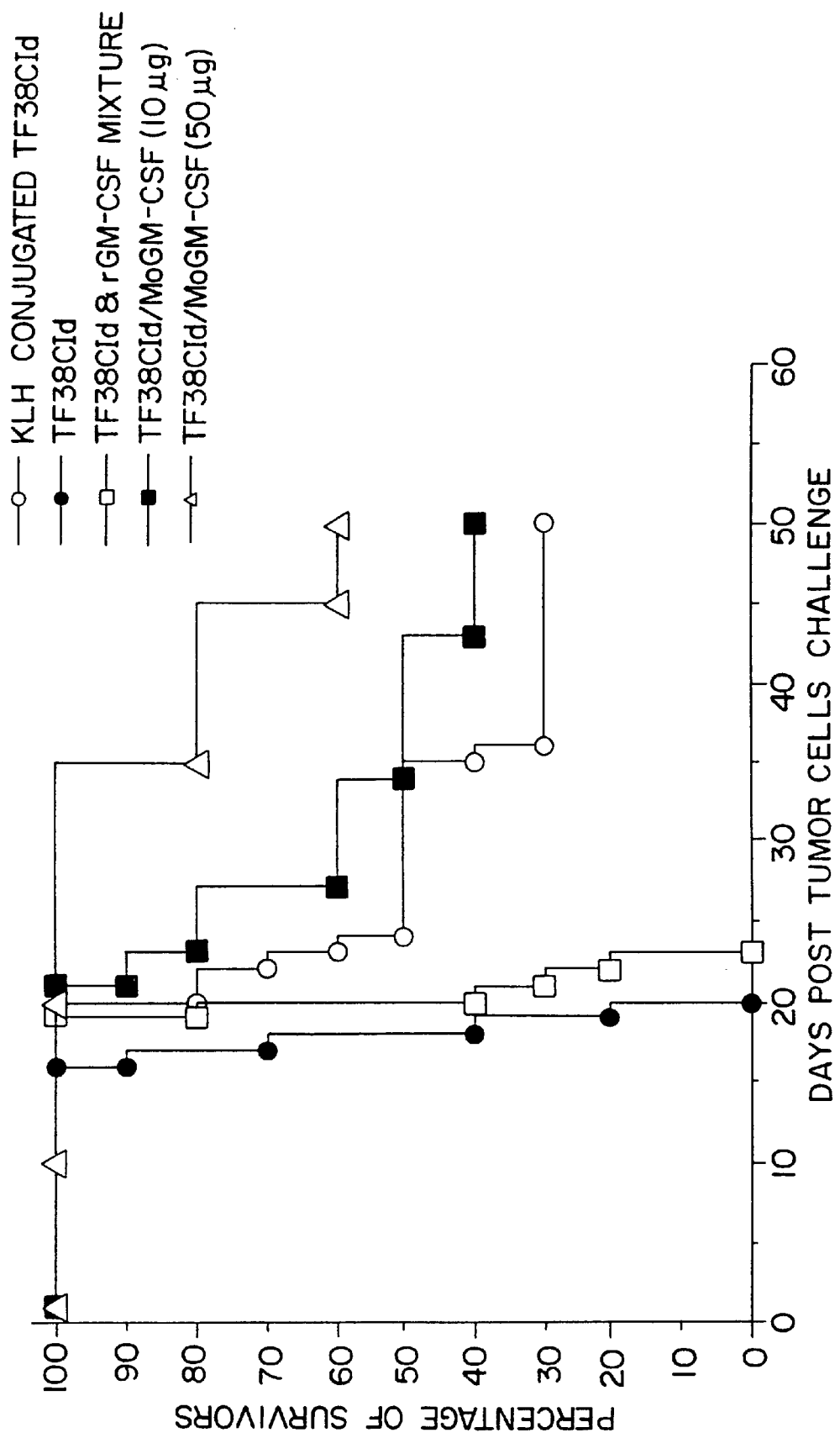
FIG. 5 is a graph showing the ability of mice immunized with the immunocomplex of the invention to resist tumor challenge.

However, the fusion protein was more successful in prolonging survival after challenge with tumor cells. At day 0, the mice were challenged with 38C13 tumor cells intraperitoneally, and the survival of the challenged mice was followed. The results are shown in FIG. 5.

Mice immunized with idiotype alone (TF38CId) or with idiotype mixed with recombinant GM-CSF (● and □, respectively) survived only 20–25 days after challenge. All animals were dead after that time. Animals immunized with KLH-conjugated idiotype (○) had a 50% survival rate at day 25 and 30% of the animals were still alive after 50 days. Mice immunized with 10 μg of fusion protein (●) had a 50% survival rate after 34 days and 40% were still alive at day 50. Mice immunized with 50 μg of the fusion protein (Δ) had a 60% survival rate at day 50.

EXAMPLE 4

Construction of Idiotype/IL-2 and IL-4 Fusion Proteins

Figure 6A:
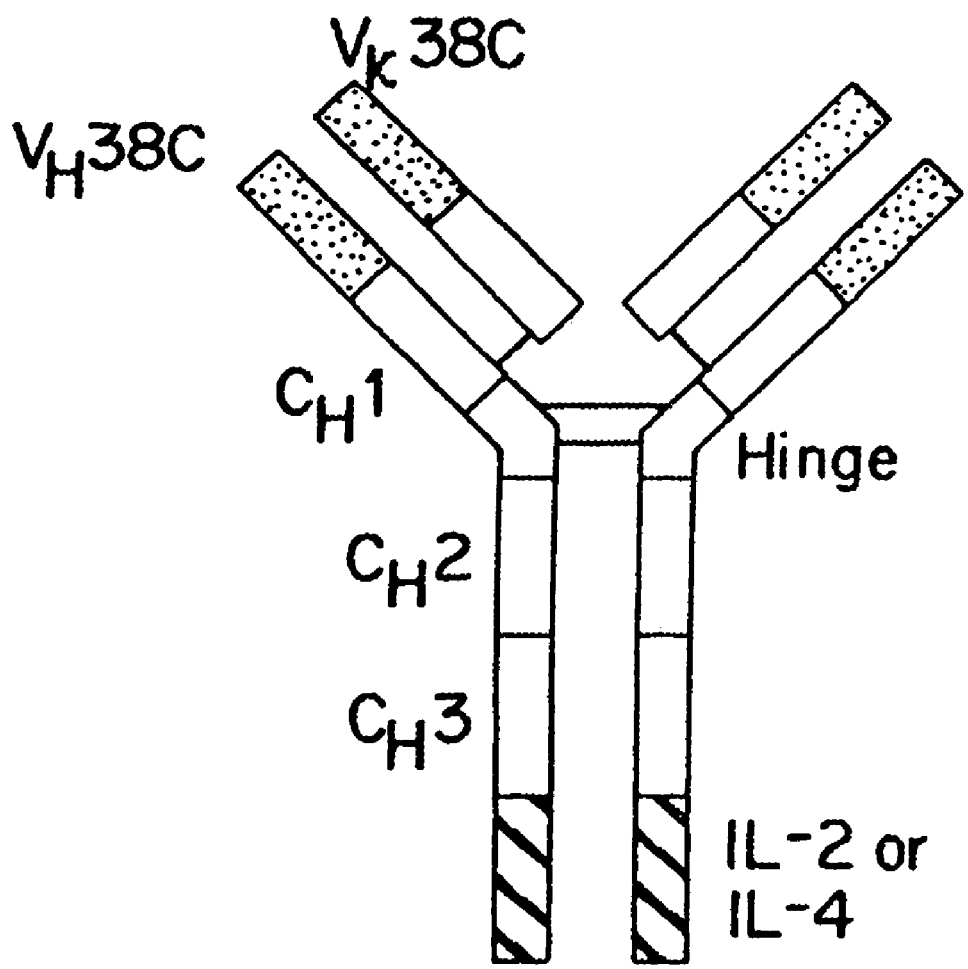
FIG. 6A shows the dimeric Id/interleukin fusion proteins.
Figure 6B:
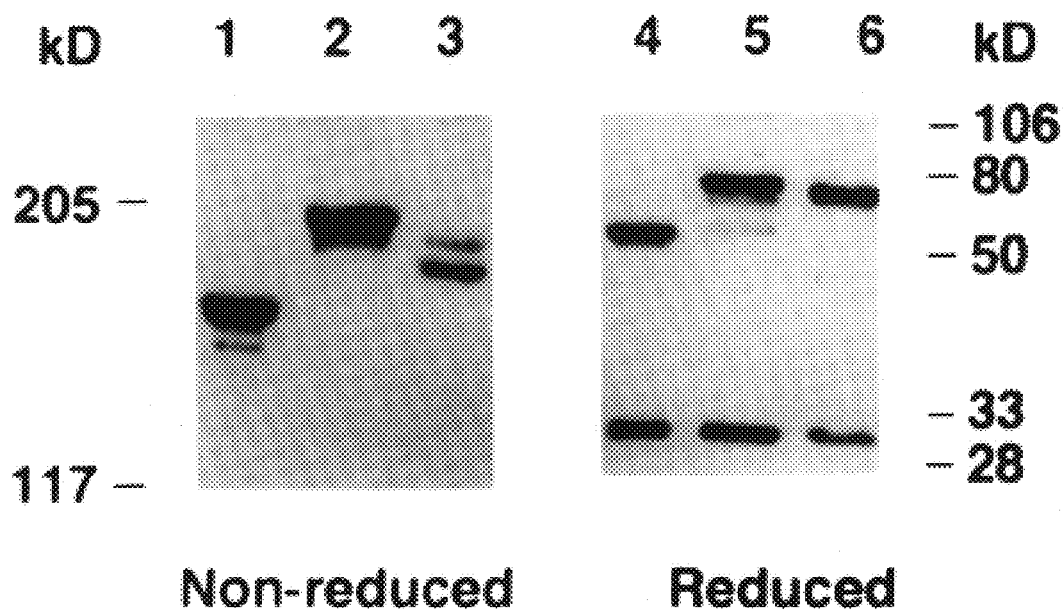
FIG. 6B is a photocopy of a photograph of the chimeric tumor idiotypic/interleukin proteins analyzed by gel electrophoresis.
Figure 6C:
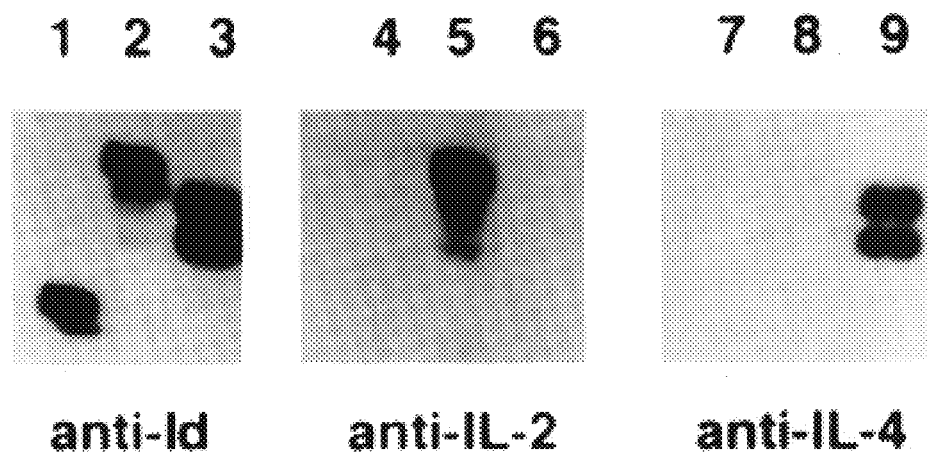
FIG. 6C is a photocopy of a photograph of the immunoblotting analysis of the chimeric idiotypic/interleukin proteins.

To make Id/MoIL-2 and Id/MoIL-4 fusion proteins, the genetic fragment encoding mature murine IL-2 or IL-4 was attached to the end of the $C_H3$ exon of the human Cγ1 gene. The resulting fusion proteins were dimeric with respect to the interleukin molecule as shown in FIG. 6A. All proteins were produced in tissue culture and purified by protein A chromatography. These chimeric tumor idiotypic proteins were analyzed by sodium dodecyl sulfate polyacrylamide gel electrophoresis (SDS-PAGE) and immunoblotting techniques. Under reducing conditions the protein bands of Id migrate with apparent mw of 30.5- and 58-kD, representing the heavy and light chains, respectively (FIG. 1B). Reduction of Id/MoIL-2 and Id/MoIL-4 also gave a 30.5-kD light chain, but both heavy chain molecules migrated slower than Id heavy chain with apparent mw of 76- and 72-kD, respectively, indicating that they contained the IL-2 or IL-4 tail. As shown in the nonreducing gel (FIG. 6B), the Id protein was secreted as a single band of mw of 160-kD. Both fusion proteins were migrated as doublets in the nonreducing gel with apparent mw of 191- and 198-kD (Id/MoIL-2) and 181- and 191-kD (Id/MoIL-4), indicating that these molecules are present in two different conformations. The immunoblotting analysis of these chimeric idiotypic proteins is shown in FIG. 6C. The results were consistent with the expected constructs of these proteins, in that the anti-Id antibody recognizes all three Id-derived molecules; in contrast, anti-IL-2 and anti-IL-4 antibodies only recognize Id/MoIL-2 and Id/MoIL-4 fusion molecules, respectively.

EXAMPLE 5

Ability of the IL Fusion Proteins to Retain Immune Enhancement

Figure 7A:
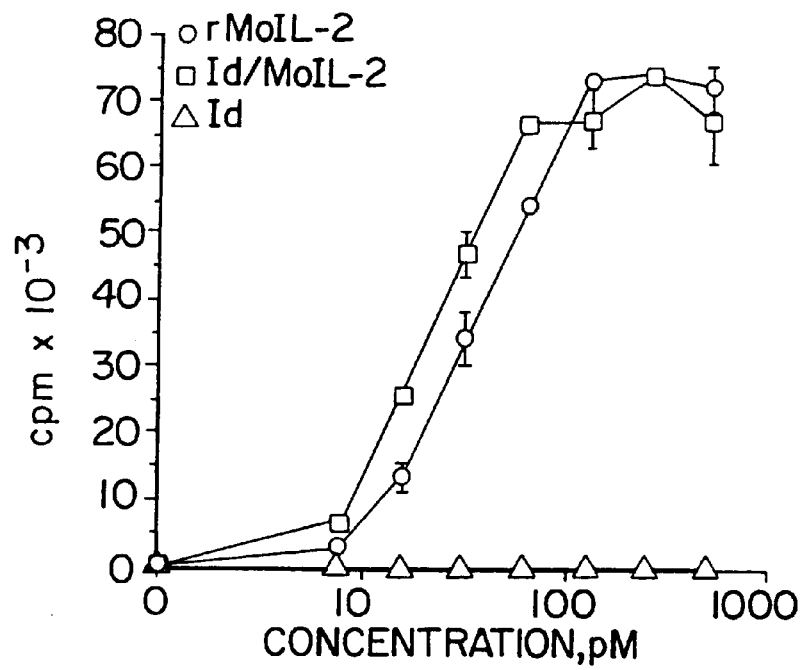
FIG. 7A shows the results of an analysis of the purified chimeric idiotypic/interleukin proteins for their ability to support the proliferation of a murine IL-2/IL-4-responsive T cell line, HT-2.
Figure 7B:
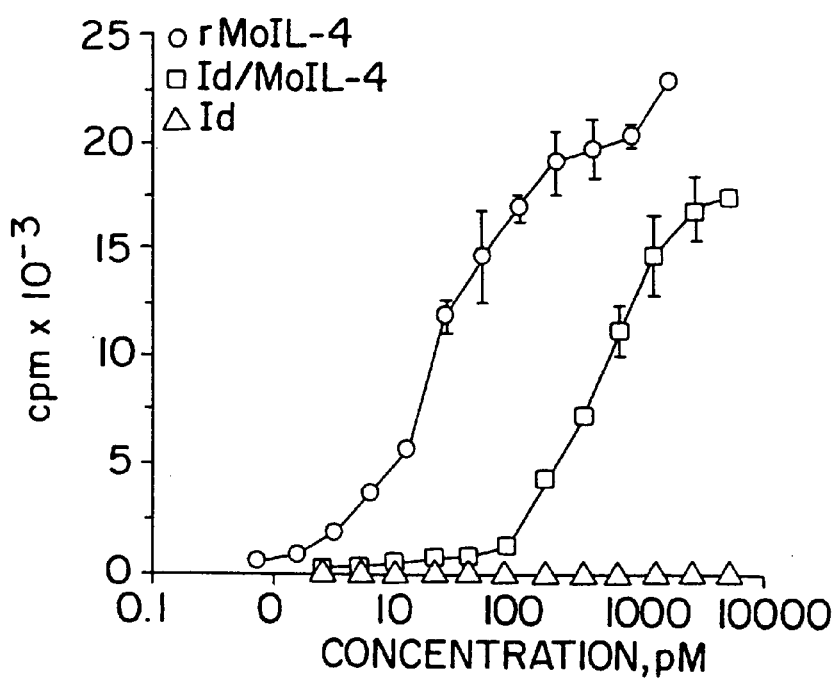
FIG. 7B is a comparison of the activity of recombinant IL-4, the idiotypic/IL-4 chimeric protein and the idiotypic antigen in the proliferation assay described above.
Figure 7C:
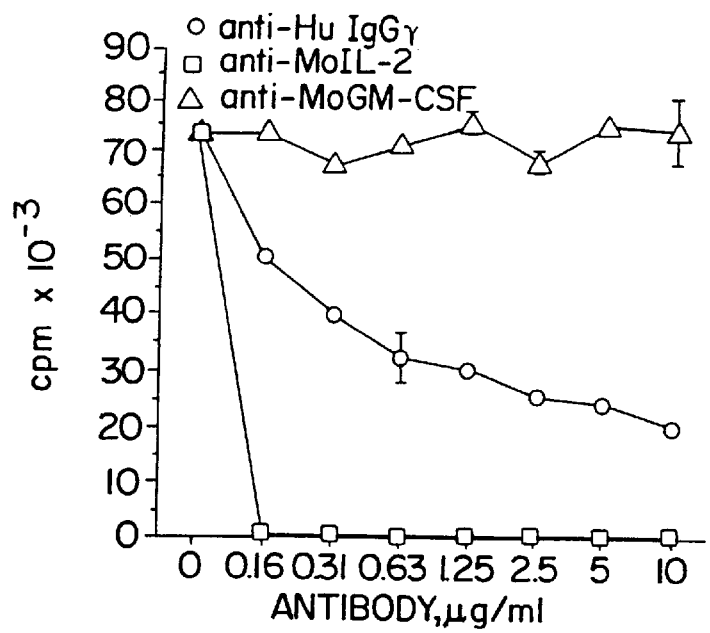
FIGS. 7C and 7D show that the activity of Id/MoIL-2 and Id/MoIL-4 was inhibited by anti-IL-2 and anti-IL-4 antibodies, respectively, but not by a control antibody.
Figure 7D:
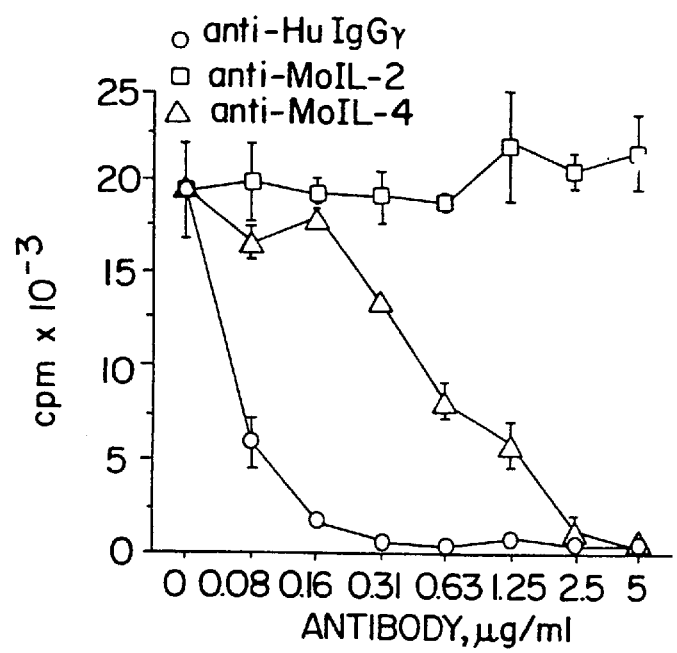

ELISA assay results showed that Id, Id/MoIL-2, and Id/MoIL-4 all reacted with four different monoclonal anti-idiotypic antibodies raised against the native murine 38C13 idiotypic protein. To determine the functional activity of the murine IL-2 or IL-4 portion of the fusion molecules, purified proteins were analyzed for their ability to support the proliferation of a murine IL-2/IL-4-responsive T cell line, HT-2. While Id was completely negative in this assay, Id/MoIL-2 clearly demonstrated the ability to stimulate the growth of HT-2 cells in a dose-dependent manner (FIG. 7A). On a per molecule basis, Id/MoIL-2 was indistinguishable from recombinant murine IL-2 in the ability to induce the proliferation of HT-2 cells. When compared to recombinant IL-4, Id/MoIL-4 fusion protein had about a 25-fold decrease in the activity (FIG. 7B). The reduction in specific activities is not explained by the low pH used for eluting Id fusion proteins from protein A Sepharose, since the activity of the Id/MoIL-4 from the transfected cell culture media and the purified protein is almost identical. Mouse IL-4 contains three sets of disulfide bonds which are important for maintaining its structure and the biological activities. Fusion of IL-4 to the immunoglobulin heavy chain may disrupt the normal disulfide pairings and thus decrease its activity. The fact that two conformational Id/MoIL-4 molecules are present in the purified proteins supports this hypothesis. FIG. 7C and 7D show that the activity of Id/MoIL-2 and Id/MoIL-4 was inhibited by anti-IL-2 and anti-IL-4, respectively, but not by a control antibody, indicating that the cytokine activity is specific. Incubation of the Id/MoIL-2 or Id/MoIL-4 with antibody against human γ-chain also arrested cell growth, indicating that the cytokine activity is in the form of a fusion molecule.

EXAMPLE 6

Ability of the IL Fusion Proteins to Immunize Mice

Anti-idiotypic antibodies were induced by immunization with different idiotypic proteins. Groups of eight- to ten-week-old female C3H/HeN mice were immunized intraperitoneally or subcutaneously with the indicated immunogens in phosphate-buffered saline unless otherwise indicated. Ten mice were included in each group. Two weeks later mice were boosted with the same antigens. KLH-Id was made by coupling KLH to Id using 0.1% glutaraldehyde#. The cytokine molarity of 1.4 µg of recombinant murine IL-2 (rMoIL-2) and 1.9 µg of rMoIL-4 was equivalent to 10 µg of Id/MoIL-2 and Id/MoIL-4, respectively. Serum was sampled by tail bleeding ten days after the last immunization. The titers of antisera against native 38C13 idiotype (IgM, κ) were determined by ELISA using a cocktail of murine antibodies [S3H5 (IgG1), S1C5 (IgG2a), S5A8 (IgG2b)] as a standard. The results are shown in Table 2. The data are expressed as the mean concentration±standard deviation (SD).

TABLE 2

| Immunogen | Dose (µg) | Anti-idiotypic antibody (µg/ml ± SD) | |
|---|---|---|---|
| | | Intraperit. | Subcutan. |
| Id | 10 | 0 | 0 |
| Id ± rMoIL-2 | 10 + 1.4 | 0 | 0 |
| Id + rMoIL-4 | 10 + 1.9 | 0 | 0 |
| KLH-Id + adj.* | 10 | 205.7 ± 39.0 | 139.8 ± 19.0 |
| Id/MoIL-2 | 10 | 18.3 ± 10.4 | 28.7 ± 16.2 |
| Id/MoIL-4 | 10 | 79.0 ± 25.6 | 45.1 ± 15.9 |

*KLH-Id was administered with the adjuvant SAF-1 in the first immunization and with incomplete SAF-1 (lacking the MDP component) in the second immunization.

Sera from animals immunized with Id and its cytokine-derived fusion proteins, either intraperitoneally or subcutaneously, were collected 10 days after the second immunization and analyzed in an ELISA for their reactivity with native 38C13 idiotypic protein. Id did not induce detectable anti-idiotypic antibodies (Table 2); thus the carrier or helper effects of human immunoglobulin constant regions were negligible. Conversely, both Id/MoIL-2 and Id/MoIL-4 induced significant amounts of anti-idiotypic antibodies in all immunized animals. Vaccination of Id/MoIL-4 via the intraperitoneal route elicited higher titers of anti-idiotypic antibodies (79.0±25.6 µg/ml) compared to that induced through the subcutaneous route (45.1±15.9 µg/ml), while no significant difference of antibody titers was found in mice immunized with Id/MoIL-2 either intraperitoneally or subcutaneously. Animals immunized with a simple mixture of Id and recombinant murine IL-2 or IL-4 produced no anti-idiotype response, indicating that fusion of the cytokine molecule to tumor idiotype was required for enhanced immunogenicity. The carrier effects of murine IL-2 or murine IL-4 in the fusion protein in the immune responses was ruled out since fusion proteins containing a similar size but biologically inert human GM-CSF or a peptide derived from the pre-S2 region of hepatitis B virus surface antigen # induced no anti-idiotypic antibodies. These results show that the fusion protein requires cytokine activity for its immune-enhancing function. Compared with mice immunized with Id chemically conjugated to the strong carrier protein keyhole limpet hemocyanin (KLH) with adjuvant, titers of anti-idiotypic antibodies induced by Id/MoIL-4 and Id/MoIL-2 were about three-fold and five- to seven-fold lower, respectively. The immune responses are specific because no reactivity occurred against other proteins such as KLH or 4C5 (an irrelevant mouse IgM). Fluorescent-activated cell sorting (FACS) analysis showed that the immune sera from mice vaccinated with Id/MoIL-2 or Id/MoIL-4 specifically recognized 38C13 tumor cells but not an immunoglobulin-negative variant.

Figure 8A:
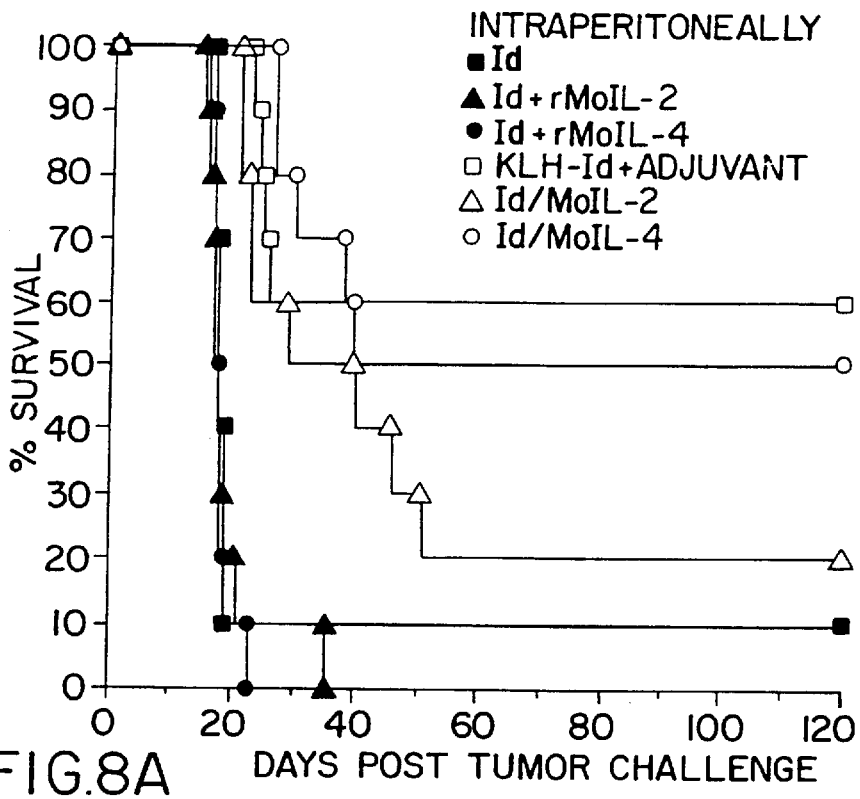
FIG. 8A illustrates that mice vaccinated intraperitoneally with Id/MoIL-2 or Id/MoIL-4 had a significantly prolonged survival time compared with mice receiving Id alone.
Figure 8B:
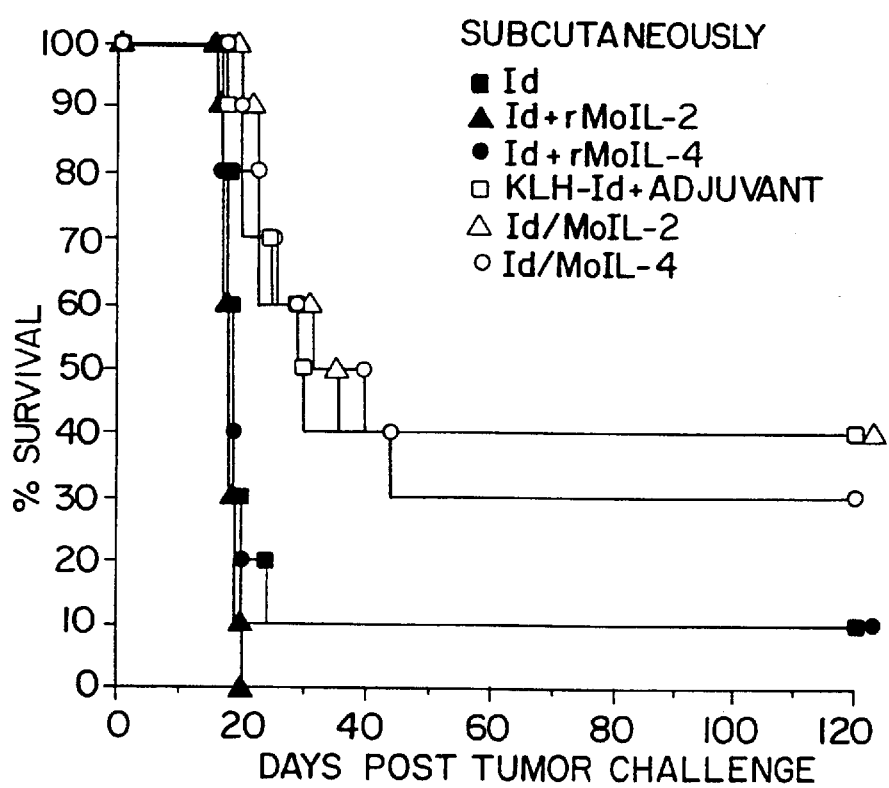
FIG. 8B illustrates that mice immunized with Id/MoIL-2 and Id/MoIL-4 also induced protective immunity and resulted in 40% and 30% long-term survivors, respectively, while vaccination with a mixture of Id and IL-2 or IL-4 yielded no protection.

Two weeks after the second immunization, mice were challenged with 38C13 tumor cells. FIG. 8A illustrates that mice vaccinated intraperitoneally with Id/MoIL-2 or Id/MoIL-4 had a significantly prolonged survival time compared with mice receiving Id alone (p<0.01 and p<0.01). 50% of Id/MoIL-4 and 20% of Id/MoIL-2 immunized animals remained tumor free for greater than 120 days, whereas vaccination with Id yielded only 10% long-term survivors. Mice immunized with Id along with recombinant IL-2 or IL-4 did not show any protection (p>0.7 and p>0.2) and all mice died of tumors before day 36. The positive control group receiving KLH-conjugated Id with adjuvant were well protected and resulted in 60% survivors (p<0.01) (FIG. 8A). Similar results were obtained from groups of mice immunized subcutaneously. As shown in FIG. 8B, mice immunized with Id/MoIL-2 and Id/MoIL-4 also induced protective immunity and resulted in 40% and 30% long-term survivors, respectively. Again, vaccination with a simple mixture of Id and IL-2 or IL-4 yielded no protection. The long-term survivors (>120 days after tumor challenge) were free of residual or dormant tumor cells by several criteria, including FACS analysis, in vitro culture and in vivo transfer of splenocytes. Tumors that did grow in the immunized animals were examined for surface idiotype expression and were found to be positive.

What is claimed is:

1. An immunocomplex consisting of a B cell lymphoma tumor-associated idiotypic immunoglobulin covalently bound directly or through a linker to an immune-enhancing cytokine, wherein said immunocomplex induces the formation of protective antibody specific to the B cell lymphoma tumor associated idiotypic immunoglobulin.

2. The immunocomplex of claim 1 wherein said B cell lymphoma tumor-associated idiotypic immunoglobulin and said immune-enhancing cytokine are coupled through a nonprotein linker.

3. The immunocomplex of claim 1 wherein said B cell lymphoma tumor-associated idiotypic immunoglobulin and said immune-enhancing cytokine are linked through a protein linker, said immunocomplex being a fusion protein.

4. The immunocomplex of claim 1 wherein the immune-enhancing cytokine is GM-CSF.

5. The immunocomplex of claim 1 wherein the immune-enhancing cytokine is IL-2.

6. The immunocomplex of claim 1 wherein the immune-enhancing cytokine is IL-4.

7. A vaccine for protecting subjects against B cell lymphoma tumor proliferation, which vaccine comprises an effective amount of the immunocomplex of claim 1 in admixture with at least one pharmaceutically acceptable excipient.

* * * * *

UNITED STATES PATENT AND TRADEMARK OFFICE
CERTIFICATE OF CORRECTION

| | |
|---|---|
| PATENT NO. | : 6,099,846 |
| DATED | : August 8, 2000 |
| INVENTOR(S) | : Ronald Levy and Mi-Hau Tao |

It is certified that error appears in the above-identified patent and that said Letters Patent is hereby corrected as shown below:

<u>Column 1,</u>
Line 11, above the "TECHNICAL FIELD" heading, please insert the following heading: -- STATEMENT REGARDING FEDERALLY SPONSORED RESEARCH OR DEVELOPMENT --; and
Above the "TECHNICAL FIELD" heading, please insert the following paragraph:
-- This invention was made with Government support under contract CA33399 awarded by the National Institutes of Health. The Government has certain rights in this invention. --.

Signed and Sealed this

Twenty-fourth Day of June, 2003

JAMES E. ROGAN
*Director of the United States Patent and Trademark Office*